(12) United States Patent
Förster

(10) Patent No.: US 7,837,465 B2
(45) Date of Patent: Nov. 23, 2010

(54) ORTHODONTIC EXPANSION SCREW

(75) Inventor: Rolf Förster, Pforzheim (DE)

(73) Assignee: Bernhard Förster Gmbh, Pforzheim (DE)

( * ) Notice: Subject to any disclaimer, the term of this patent is extended or adjusted under 35 U.S.C. 154(b) by 138 days.

(21) Appl. No.: 12/004,207

(22) Filed: Dec. 20, 2007

(65) Prior Publication Data

US 2008/0171300 A1   Jul. 17, 2008

(30) Foreign Application Priority Data

Jan. 13, 2007   (DE) .................. 10 2007 002 040

(51) Int. Cl.
*A61C 3/00*   (2006.01)
(52) U.S. Cl. ......................................... 433/7
(58) Field of Classification Search ............. 433/7; 74/816; 188/83, 381, 77 R; 411/979
See application file for complete search history.

(56) References Cited

U.S. PATENT DOCUMENTS

| | | | |
|---|---|---|---|
| 3,742,552 A * | 7/1973 | Balchunas | ................ 16/42 R |
| 5,281,133 A | 1/1994 | Farzin-Nia | |
| 6,109,916 A * | 8/2000 | Wilcko et al. | ................ 433/24 |
| 6,328,745 B1 * | 12/2001 | Ascherman | ................ 606/86 R |
| 6,783,361 B2 * | 8/2004 | Huge et al. | ................ 433/7 |
| 7,384,265 B2 * | 6/2008 | Hanks | ................ 433/7 |
| 2004/0214126 A1 | 10/2004 | Förster et al. | |
| 2005/0037313 A1 | 2/2005 | Huge et al. | |

FOREIGN PATENT DOCUMENTS

DE   10 2004 019 524 A1   11/2004

* cited by examiner

*Primary Examiner*—Ralph A Lewis
(74) *Attorney, Agent, or Firm*—Walter A. Hackler

(57) ABSTRACT

An orthodontic expansion screw having two bodies whose distance from each other can be changed by means of a spindle that engages both bodies. The spindle includes an actuation part for effecting a torque for readjusting the spindle, and a straight-line guide for engaging both bodies and guiding the bodies along two guide axes that are parallel to each other while preventing a relative rotation of the bodies when their distance from each other is being changed. A friction brake is provided that presses onto the actuation part of the spindle and thus generates a frictional force that renders a rotation of the spindle in both directions of rotation more difficult in order to prevent inadvertent readjustment of the spindle.

14 Claims, 3 Drawing Sheets

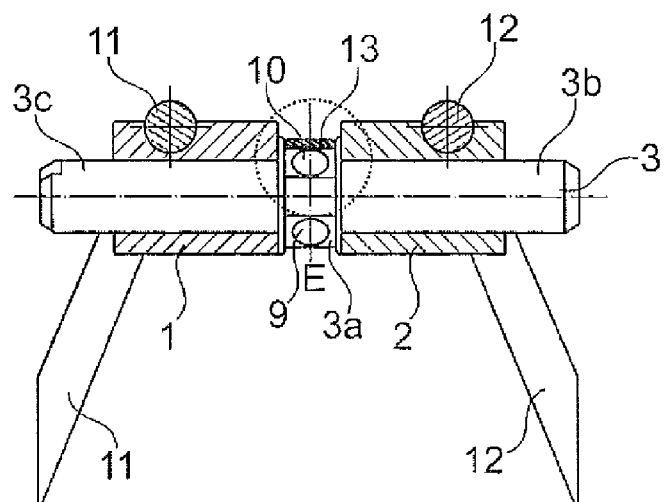
Fig. 3
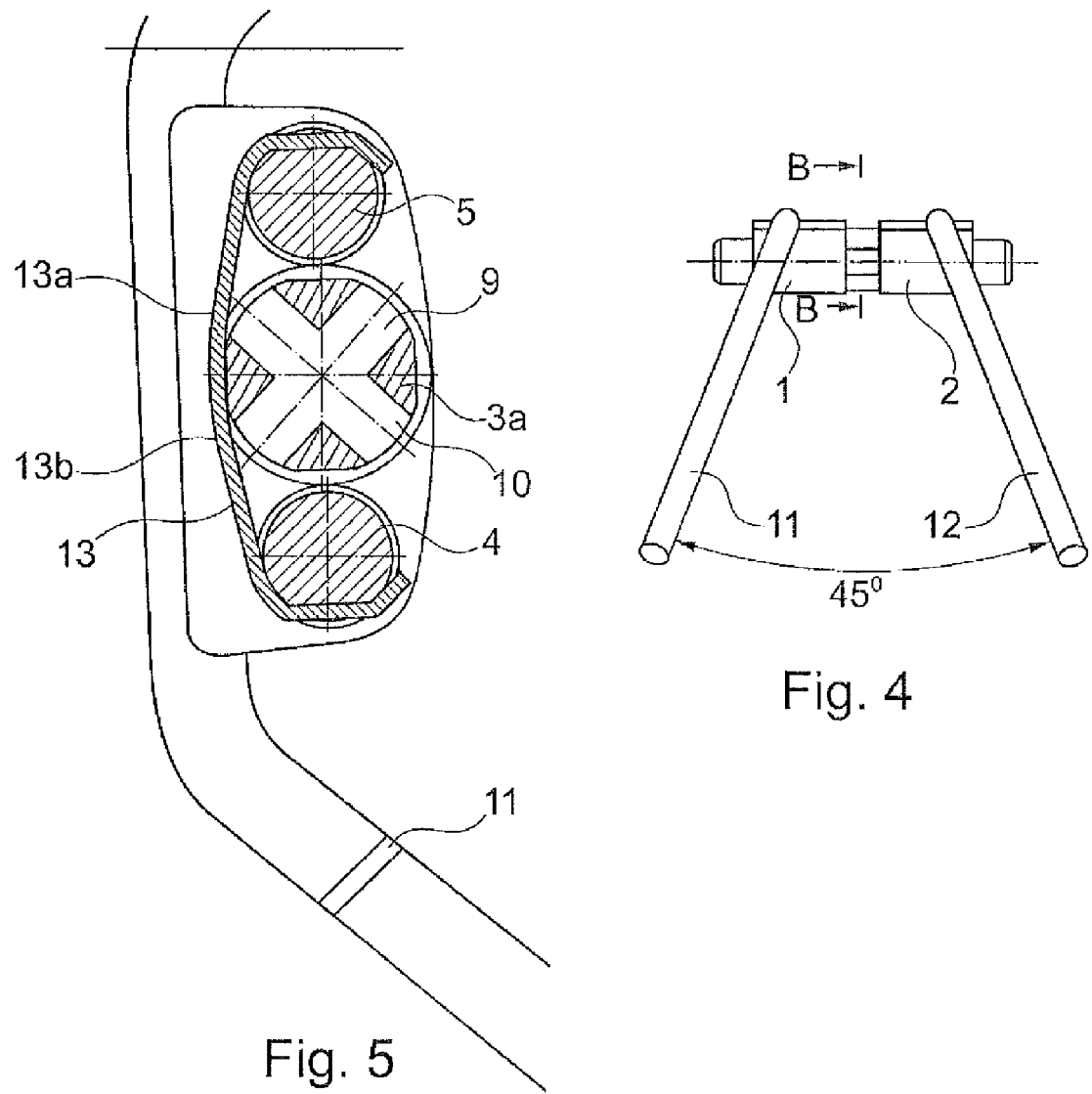
Fig. 4
Fig. 5

ORTHODONTIC EXPANSION SCREW

The invention relates to an orthodontic expansion screw. An expansion screw of this type for correcting malpositions of teeth is known, for example, from DE 102004019524 A1.

For the treatment progress in correcting a malposition of teeth to be achieved through the use of an expansion screw, it is important for the spindle to remain in the position to which the attending orthodontist rotated it without the screw self-readjusting in the mouth. For this reason, orthodontic expansion screws have an impediment to prevent inadvertent readjustment of the spindle.

For example, an expansion screw is known from US 2005/0037313 A1 in which the impediment is formed by a combination of a ratchet and a pawl such that the expansion screw is kept from rotating backwards by means of a form-fit. However, an impediment of this type is disadvantageous in that residual food particles and dental calculus may become deposited easily on the angled surfaces of the ratchet and pawl such that these are difficult to clean. Moreover, the manufacture of an impediment of this type is resource-consuming.

Moreover, the prior art also knows to realize an impediment by making the thread of the spindle sluggish. For example, the internal screw thread of the expansion screw bodies that are engaged by a thread part of the spindle can be squeezed slightly. This is disadvantageous in that the extension of an impediment thus generated is difficult to reproduce such that there are considerable differences in impediment within a set of expansion screws.

SUMMARY OF THE INVENTION

It is therefore the object of the invention to devise a way of realizing an impediment that facilitates an expansion screw that is easy to clean and can be manufactured in a cost-efficient manner.

This object is met according to the invention by a friction brake that presses onto the actuation part of the spindle and thereby generates a frictional force that renders a rotation of the spindle in both directions of rotation more difficult in order to prevent inadvertent readjustment of the spindle.

A friction brake according to the invention can, for example, be realized in the form of a metal part that rests on the actuation part. A suitable metal part, for example a shackle or metal strip, is cost-efficient and, because its surface is smooth, easy to clean.

The actuation part of an expansion screw according to the invention preferably comprises through bore holes intended for insertion of an adjustment tool in order to readjust the spindle. A friction brake according to the invention can be used to cover the side of the actuation part that faces the palate such that the palate is protected from being prodded by a readjustment tool that is inserted in the bore hole.

BRIEF DESCRIPTION OF THE DRAWINGS

Further details and advantages of the invention are illustrated in the following by means of exemplary embodiments and by making reference to the appended drawings. Identical and equivalent components are labeled by identical reference numbers in the drawings. In the figures:

FIG. 3 shows a sectional view along the section line CC of FIG. 2;

FIG. 4 shows a side view of the exemplary embodiment shown;

FIG. 5 shows a sectional view along the section line BB of FIG. 4;

DETAILED DESCRIPTION

Figure 1:
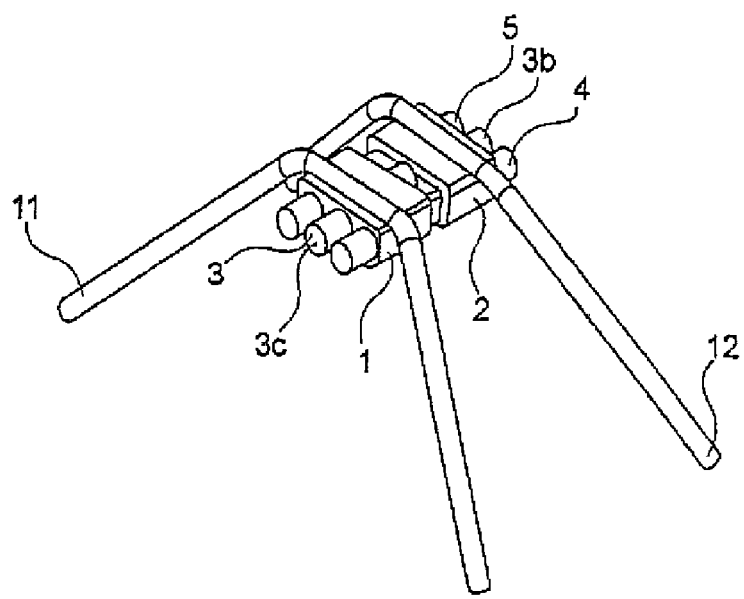
FIG. 1 shows an oblique view of an exemplary embodiment of an expansion screw according to the invention.
Figure 2:
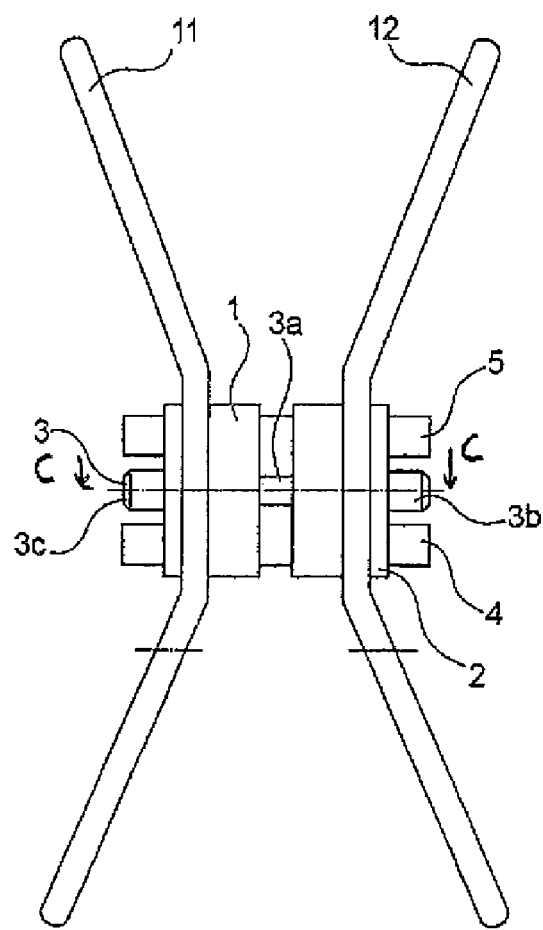
FIG. 2 shows a top view of the exemplary embodiment shown.

FIGS. 1 and 2 show an expansion screw having a symmetrical structure and two bodies 1, 2 whose distance from each other can be changed by means of a spindle 3, which has, in its middle, an actuation part 3a and, originating therefrom and extending in opposite direction, two thread parts 3b and 3c having opposite direction of turn. The thread parts 3b, 3c each are suspended in one of the bodies 1, 2 such that they are capable of being rotated, and engage an internal thread therein. Two cylindrical guide pins 4, 5 are provided on two sides of the spindle 3 and are inserted in matching through bore holes of the two bodies 1 and 2, whereby pairs of said bore holes are in alignment with each other. The guide pins 4, 5 form straight-line guiding means that guide the two bodies 1, 2 along two guide axes that are parallel to each other while preventing a relative rotation of the bodies when their distance from each other is changed.

Suitable straight-line guiding means can, as a matter of principle, also be formed by the spindle 3 itself and a single guide pin, however, embodiments having two guide pins are preferred because of their more symmetrical introduction of the force generated by the spindle 3 into the two bodies 1, 2. Moreover, it is also feasible, as a matter of principle, to use a spindle having just a single thread part instead of a spindle having two thread parts 3b, 3c, i.e. to connect to only one of the bodies 1, 2 in a rotatable manner and to connect to the other body in a rigid manner.

The actuation part 3a has two transverse bore holes 9, 10 that intersect at a right angle and can be seen, in particular, in the longitudinal and transverse sectional views of FIGS. 3 and 5. A readjustment tool, for example a pin, is intended to be inserted in the bore holes 9, 10 for readjustment of the spindle 3. Readjustment of the actuation part 3a changes the distance between the two bodies 1, 2, which glide on the guide pins 4, 5 in the process, such that the two bodies 1 and 2 are guided in a straight line and a relative rotation of the two bodies 1 and 2 with respect to each other is prevented.

The expansion screw has four retention arms 11, 12 with two of which each being attached to one of the bodies 1 or 2. Expansion screws, in particular palatinal split screws, such as the exemplary embodiment shown, are commercially available in a form having angled retention arms that are adjusted by the attending orthodontist to match the assembly situation in the mouth of the patient.

In order for the expansion screw to not self-readjust in the jaw of a patient, the expansion screw shown has an impediment which, in the exemplary embodiment shown, is formed by a friction brake 13 that is shown, in particular, in FIG. 5 and presses onto the actuation part 3a of the spindle 3 and by this means generates a frictional force that renders a rotation of the spindle 3 in both directions of rotation more difficult. FIG. 5 shows a cross-sectional view of the expansion screw along the section line BB of FIG. 4. Herein is shown that the friction brake 13 presses in radial direction onto the actuation part 3a and rests on a lateral surface of the actuation part 3a.

In the exemplary embodiment shown, the friction brake 13 is provided in the form of a metal ribbon that extends transverse to the guide axes over the spindle 3 and is connected to the two guide pins 4, 5, preferably by means of welding. The friction brake 13 covers the side of the actuation part 3*a* which in use faces the palate, and thus protects a patient from being injured during readjustment of the expansion screw by a pin that is inserted in one of the transverse bore holes 9, 10.

The external cross-section of the actuation part 3*a* of the spindle 3 deviates from a circular shape such that the frictional force generated by the friction brake 13 is a function of the spindle's 3 angular position of rotation. In the exemplary embodiment shown, this deviation from a circular shape is generated by the actuation part 3*a* comprising flattened areas that extend between the bore holes 9, 10, in the direction of the circumference. Upon readjustment of the spindle 3, the metal ribbon forming the friction brake 13 is stretched because the external cross-section of the actuation part 3*a* deviates from a circular shape. This leads to an increased frictional force that can be easily overcome by a readjustment tool that is inserted in one of the bore holes 9, 10, but reliably prevents inadvertent readjustment. Since the friction brake 13 gets slightly stretched each time the spindle 3 is readjusted, it is useful to provide it in the form of a spring element, such as a leaf or shackle spring.

Having the external cross-section of the actuation part 3*a* deviate from a circular shape is advantageous, in particular, in that an orthodontist readjusting the spindle 3 can feel when a rotation angle step is completed by means of the increase and subsequent decrease in the frictional resistance. To have an external cross-section deviate from a circular shape allows catching positions to be defined that are characterized by a maximal static frictional force. Readjusting the spindle 3, an orthodontist can feel how an increased force is required initially in order to somewhat stretch the metal ribbon 13 forming the friction brake. As soon as half of a readjustment step is completed, in the exemplary embodiment shown, this corresponds to a rotation by 45° from the catching position shown in FIG. 5, the force required to rotate the spindle decreases noticeably and further rotation of the spindle up to the next catching position is then supported by the spring force stored in the friction brake.

In the exemplary embodiment shown, the metal ribbon forming the friction brake 13 has two kinks 13*a*, 13*b* that border a bearing surface by means of which the friction brake 13, being in the catching position shown in FIG. 5, touches against one of the flattened areas of the actuation part 3*a*. The kinks 13*a*, 13*b* cause the metal ribbon forming the friction brake 13, being in a catching position, to bear on the actuation part 3*a* in a planar fashion. By this means, an orthodontist can feel even better when a catching position is reached during readjustment of the spindle 3.

Figure 6:
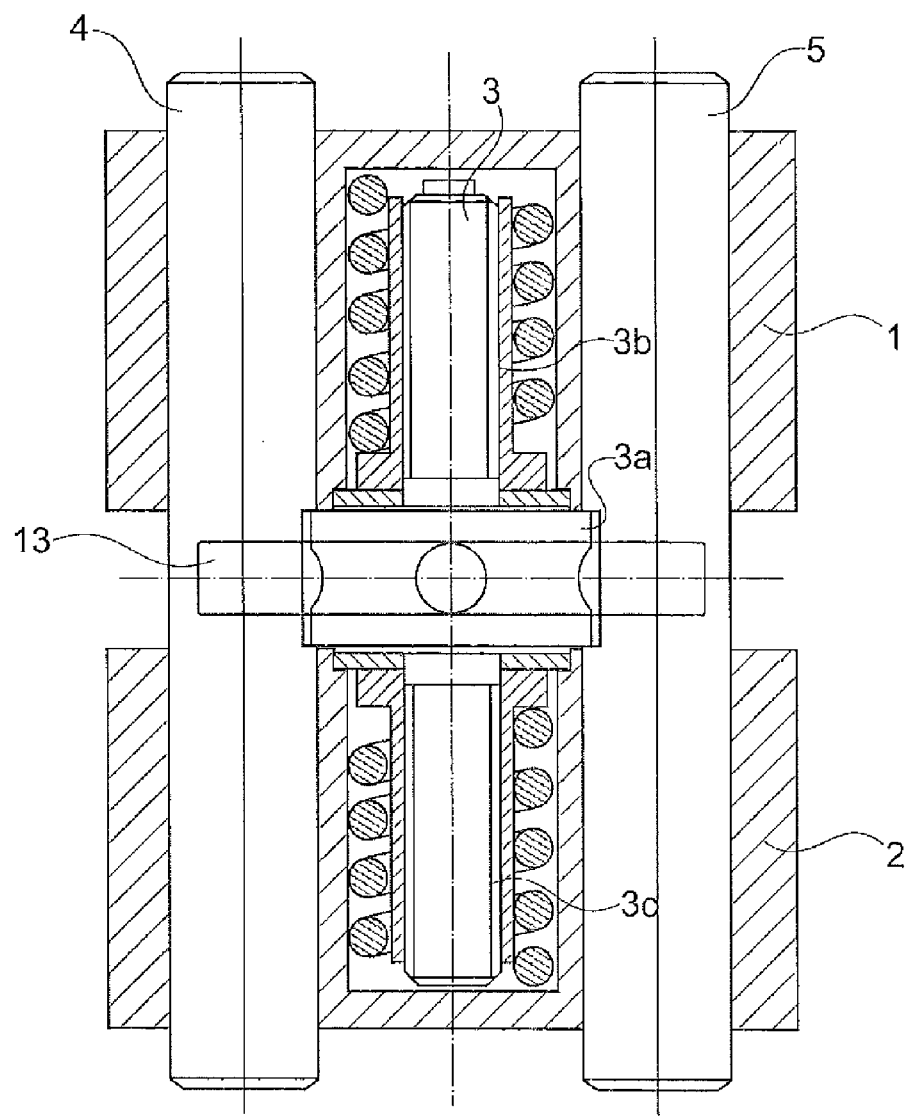
FIG. 6 shows another exemplary embodiment of an expansion screw according to the invention.

FIG. 6 shows another exemplary embodiment of an expansion screw according to the invention. In this exemplary embodiment, the spindle 3 does not extend through the two bodies 1, 2, but rather is pinned-in in pocket holes. Similar to the preceding exemplary embodiment described above, the friction brake 13 is realized in the form of a metal ribbon that extends transverse to the guide axes over the actuation part 3*a* of the spindle 3 and is connected at its two ends to the guide pins by a substance-to-substance bond.

Figure 7:
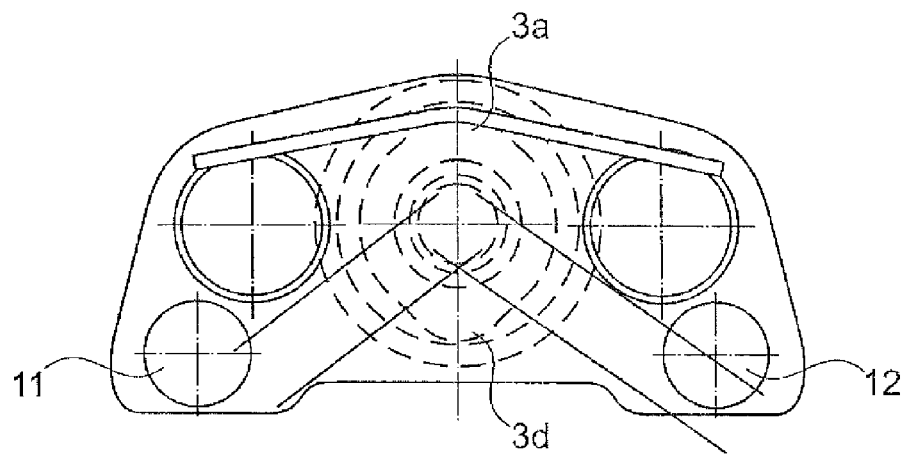
FIG. 7 shows a schematic side view related to FIG. 6 with the direction of view being along the spindle.

FIG. 7 shows a schematic view of the exemplary embodiment shown in FIG. 6 with the direction of view being along the spindle 3. The figure shows that the cross-section of the actuation part 3*a* deviates from a circular shape since it comprises two humps 3*d* that are arranged between the transverse bore holes. Similar to the flattened areas of the actuation part 3*a* in the preceding exemplary embodiment, these humps 3*d* cause the frictional force generated by the friction brake to be a function of the rotational angle of the spindle 3.

LIST OF REFERENCE NUMBERS

1. Body
2. Body
3 Spindle
3*a* Actuation part
3*b* Thread part
3*c* Thread part
3*d* Hump
4 Guide pin
5 Guide pin
9 Transverse bore hole
10 Transverse bore hole
11 Retention arm
12 Retention arm
13 Friction brake
13*a* Kink
13*b* Kink

What is claimed is:

1. Orthodontic expansion screw comprising:
   two bodies whose distance from each other can be changed by means of a spindle that engages both bodies, whereby the spindle comprises an actuation part by means of which a torque can be effected for readjusting the spindle;
   straight-line guiding means for engaging both bodies and guiding the bodies along two guide axes that are parallel to each other while preventing a relative rotation of the bodies when their distance from each other is being changed, the guiding means including two guide pins disposed parallel to the spindle and on opposite sides thereof; and
   a friction brake including a metal ribbon extending transverse to the guide axis over the spindle and connected to the two guide pins, the ribbon pressing onto the actuation part of the spindle for generating a frictional force that renders a rotation of the spindle in both directions of rotation more difficult in order to prevent inadvertent readjustment of the spindle,
   wherein the actuation part has two transverse bore holes that intersect at a right angle and the external cross-section of the actuation part deviates from a circular shape such that the frictional force generated by the friction brake depends on the spindle's angular position of rotation.

2. Expansion screw according to claim 1, wherein the friction brake presses onto the actuation part in radial direction.

3. Expansion screw according to claim 1, wherein the friction brake is provided in the form of a metal ribbon.

4. Expansion screw according to claim 1, wherein the friction brake presses onto a lateral surface of the actuation part.

5. Expansion screw according to claim 1, wherein the straight-line guiding means include at least two guide pins that are parallel to the spindle.

6. Expansion screw according to claim 1, wherein the friction brake is attached to at least one of the guide pins.

7. Expansion screw according to claim 6, wherein the friction brake is attached to both guide pins.

8. Expansion screw according to claim 1, wherein the actuation part comprises flattened areas that extend in the direction of the circumference.

9. Expansion screw according to claim 8, wherein the friction brake comprises a flat bearing section matching the flattened areas through which it bears on one of the flattened areas of the actuation part in a planar fashion in order to impede readjustment of the spindle.

10. Expansion screw according to claim 9, wherein the actuation part comprises at least two through bore holes for insertion of a readjustment tool in order to readjust the spindle.

11. Expansion screw according to claim 10, wherein the flattened areas are arranged between the bore holes.

12. Expansion screw according to claim 1, wherein the friction brake covers a side of the actuation part which is intended to face the palate.

13. Expansion screw according to claim 1 wherein the actuation part comprises flattened areas that extend in the direction of the circumference.

14. An orthodontic expansion screw comprising:

two bodies;

a rotatable spindle engaging the bodies for changing a distance therebetween, the spindle having an actuation part with a non-circular cross section;

a pair of parallel guide pins for stabilizing the bodies during change of distance therebetween; and a brake disposed in frictional engagement with the spindle actuating part and enabling bi-directional rotation of the spindle with a frictional force depending on an angular position of the spindle actuation part, said brake including a metal ribbon extending transversely over the spindle and connected to the guide pins.

* * * * *